(12) United States Patent
Hendrich

(10) Patent No.: US 7,682,308 B2
(45) Date of Patent: Mar. 23, 2010

(54) METHOD AND SYSTEM FOR ASSESSING FALL RISK

(75) Inventor: Loretta Ann Hendrich, Ladue, MO (US)

(73) Assignee: AHI of Indiana, Inc., Clayton, MO (US)

( * ) Notice: Subject to any disclaimer, the term of this patent is extended or adjusted under 35 U.S.C. 154(b) by 68 days.

(21) Appl. No.: 11/850,826

(22) Filed: Sep. 6, 2007

(65) Prior Publication Data

US 2008/0009686 A1 Jan. 10, 2008

Related U.S. Application Data

(62) Division of application No. 11/059,435, filed on Feb. 16, 2005, now Pat. No. 7,282,031.

(51) Int. Cl.
*A61B 5/00* (2006.01)
(52) U.S. Cl. .............................. 600/300; 128/920; 705/2
(58) Field of Classification Search ................. 600/300, 600/301; 128/903–905, 920
See application file for complete search history.

(56) References Cited

U.S. PATENT DOCUMENTS

| | | | |
|---|---|---|---|
| 5,544,649 | A | 8/1996 | David et al. |
| 5,724,379 | A | 3/1998 | Perkins et al. |
| 5,796,759 | A | 8/1998 | Eisenberg et al. |
| 5,953,704 | A | 9/1999 | McIlroy et al. |
| 6,059,724 | A | 5/2000 | Campell et al. |
| 6,154,726 | A | 11/2000 | Rensimer et al. |
| 6,223,164 | B1 | 4/2001 | Seare et al. |
| 6,246,975 | B1 | 6/2001 | Rivonelli et al. |
| 6,266,645 | B1 | 7/2001 | Simpson |

(Continued)

FOREIGN PATENT DOCUMENTS

GB 2352815 A 2/2001

OTHER PUBLICATIONS

WC. Graafmans et al., Falls in the Elderly: A Prospective Study of Risk Factors and Risk Profiles, American Journal of Epidemiology, vol. 143, No. 11, 1996, pp. 1129-1136.

(Continued)

*Primary Examiner*—Henry M Johnson, III
*Assistant Examiner*—Kai Rajan
(74) *Attorney, Agent, or Firm*—Bose McKinney & Evans LLP

(57) ABSTRACT

A method and system for determining the fall risk of a patient is provided. The method includes the evaluation of a patient to determine whether the patient exhibits one or more intrinsic fall risk factors selected from a group consisting of confusion, depression, altered elimination, dizziness, male gender, anti-epileptic/anticonvulsant prescriptions and benzodiazepine prescriptions. A specific point value is assigned to each of the intrinsic risk factors found to be exhibited by the patient. A mobility test is also performed on the patient to evaluate the patient's ability to rise from a seated position, and a specific mobility test point value is assigned to the patient based upon the patient's performance of the mobility test. Each intrinsic risk factor's specific point value is then summed together with the specific mobility test point value to achieve a total risk score, and the patient's fall risk is determined based on the total risk score. An intervention process may be developed for the patient based on the patient's fall risk.

11 Claims, 6 Drawing Sheets

U.S. PATENT DOCUMENTS

| | | | |
|---|---|---|---|
| 6,269,339 | B1 | 7/2001 | Silver |
| 6,289,299 | B1 | 9/2001 | Daniel, Jr. et al. |
| 6,317,700 | B1 | 11/2001 | Bagne |
| 6,317,731 | B1 | 11/2001 | Luciano |
| 6,468,210 | B1 | 10/2002 | Iliff |
| 2002/0004725 | A1 | 1/2002 | Martin et al. |
| 2002/0123906 | A1 | 9/2002 | Goetzke et al. |
| 2002/0169635 | A1 | 11/2002 | Shillingburg |
| 2005/0065813 | A1* | 3/2005 | Mishelevich et al. ............ 705/2 |

OTHER PUBLICATIONS

George F. Fuller, Falls in the Elderly, American Family Physician, vol. 61, No. 7, Apr. 1, 2000. (16 pages).

Patricia Schroeder: Journal of Nursing Quality Assurance, Assuring Patient Safety: vol. 3, Issue 1, Nov. 1988 (pp. 28-36).

Ann Hendrich et al.: Hospital Falls: Development of a Predictive Model for Clinical Practice: Applied Nursing Research, vol. 8, No. 3, Aug. 1995 (pp. 129-139).

Hendrich, A.L., Bender, P.S., & Nyhuis, A. (2003). Validation of the Hendrich II Fall Risk Model: A large concurrent case/control study of hospitalized patients. *Applied Nursing Research*, 16(1), 9-21. 267, 2002.

* cited by examiner

| Risk Factor | Definition | Points | Score |
|---|---|---|---|
| Confusion Disorientation Impulsivity | Patient is disoriented to time, place, and/or person. Patient is unable to retain or receive instructions or displays impaired judgment. This may be a progressive neurological state, drug induced, or behavioral in origin. Stroke patients (left hemi) may exhibit impulsive, unpredictable behavior as a result of the cerebral insult | 4 | |
| Symptomatic Depression | Medical diagnosis or nursing assessment finds the patient appears depressed, is not interacting appropriately, is tearful, withdrawn, or the patient states they are depressed. If the depression is managed with drugs and/or therapies it need NOT be scored if the depression is therapeutically in control. | 2 | |
| Altered Elimination | Altered elimination from the clinical norm, such as incontinence, nocturia, frequency, urgency or stress incontinence, diarrhea, or related to use of cathartics. This does NOT include a Foley or indwelling catheter UNLESS it causes symptoms referenced above while in use with the patient. When the catheter is removed, it can be a high-risk time until normal elimination is established. | 1 | |
| Dizziness Vertigo | Medical diagnosis of vertigo or the patient reports they feel like they are spinning or the room is spinning. Sway path may be present when the patient stands (circular motion upon arising). This is often seen in the aging adult with poor gait and balance and can occur as a result of some drug side effects. | 1 | |
| Gender | Male | 1 | |
| Any Prescribed Antiepileptics | Carbamazepine, Divalproex Sodium, Ethotoin, Ethosuximide, Felbamate, Fosphenytoin, Gabapentin, Lamotrigine, Mephenytoin, Methsuximide, Phenobarbitol, Phenytoin, Primidone, Topiramate, Trimethadione, Valproic Acid | 2 | |
| Any Prescribed Benzodiazepines | Alprazolam, Buspirone, Chlordiazepoxide, Clonazepam, Clorazepate Dipotassium, Diazepam, Flurazepam, Halazepam, Lorazepam, Midazolam, Oxazepam, Temazepam, Triazolam | 1 | |
| Get Up & Go Test | | | |
| With patient sitting in a chair (preferred) or on the side of the bed, place palm of hands flat on thighs and ask the patient to stand without assistance. Score the patient according to the guidelines below. * If the patient is unable to perform the test (unconscious, drug-induced coma, traction, debilitation/atrophy, bed rest order) score all other risk factors that *can* be assessed. If the patient scores a 5 or greater (without the Get Up and Go) and can ATTEMPT to get up they should be considered "high risk for falls" | | | |
| Ability to rise in a single movement | | 0 | |
| Pushes up, successful in one attempt | | 1 | |
| Multiple attempts, but successful | | 3 | |
| Unable to rise without assistance during test (OR if a medical order states the same and/or complete bed rest is ordered) | | 4 | |
| | | TOTAL SCORE | |

FIG. 1

| RISK FACTOR (>5 - HIGH RISK) | RISK POINTS | |
|---|---|---|
| CONFUSION/DISORIENTATION (MIXED DEFINITION)* | 4 | |
| DEPRESSION (MIXED DEFINITION)† | 2 | |
| ALTERED ELIMINATION‡ | 1 | |
| DIZZINESS/VERTIGO (SUBJECTIVE DEFINITION)§ | 1 | |
| GENDER | 1 | |
| ANY PRESCRIBED ANTIEPILEPTICS | 2 | |
| ANY PRESCRIBED BENZODIAZEPINES | 1 | |
| GET-UP-AND-GO TEST ITEM #2: "RISING FROM CHAIR" | | |
| ABILITY TO RISE IN A SINGLE MOVEMENT | 0 | |
| PUSHES UP, SUCCESSFUL IN ONE ATTEMPT | 1 | |
| MULTIPLE ATTEMPTS, BUT SUCCESSFUL | 3 | |
| UNABLE TO RISE WITHOUT ASSISTANCE | 4 | |
|  | TOTAL | |

* CHARTED AS CONFUSED OR DISORIENTED OR SCORED < 17 ON MINI-MENTAL EXAM
† CHARTED AS DEPRESSED OR SCORED >8 ON DEPRESSION TEST
‡ CHARTED WITH ALTERED ELIMINATION NEEDS OR ANSWERED "YES" TO ANY BET QUESTIONS
§ CHARTED WITH DIZZINESS OR VERTIGO

FIG. 2

Hendrich II Fall Risk - ZOELLNER, BETH CERNER

*Performed on: 01/31/2005  1035  CST                By: Riggins, Barb

Hendrich II Fall Risk Assessment

| Confusion Disorientation | ● Yes ○ No | Yes response scores 4 | Depression | ○ Yes ○ No | Yes response scores 2 |

| Altered Elimination | ○ Yes ○ No | Yes response scores 1 | Dizziness/Vertigo | ○ Yes ○ No | Yes response scores 1 |

| Gender, Male | ○ Yes ● No | Yes response scores 1 | Any Prescribed Antiepileptics | ○ Yes ○ No | Yes response scores 2 |

| Any Prescribed Benzodiazepines | ○ Yes ○ No | Yes response scores 1 | Rising From Chair (Get Up and Go Test) | ○ Able to rise in a single movement — 1 points<br>○ Pushes up, successful in one attempt — 2 points<br>○ Multiple attempts but successful — 3 points<br>○ Unable to rise without assistance — 4 points |

Hendrich II Fall Risk Score: [    ]   A score greater than or equal to 5 will automatically enter a fall risk protocol In Progress

FIG. 6

METHOD AND SYSTEM FOR ASSESSING FALL RISK

RELATED APPLICATIONS

This application is a divisional of U.S. patent application Ser. No. 11/059,435, filed Feb. 16, 2005, now U.S. Pat. No. 7,282,031, issued Oct. 16, 2007, the complete disclosure of which is hereby expressly incorporated herein by this reference.

TECHNICAL FIELD

The present invention generally relates to a new method and system for patient care, and especially a method and system for assessing and identifying individuals who are at risk for having a fall.

BACKGROUND OF THE INVENTION

Patient falls are a commonly occurring adverse event routinely reported by acute and long-term care facilities. These falls may result in patient morbidity, mortality, and even a patient's fear of falling again. In elderly patients, this fear of falling tends to restrict the patient's activities and mobility, which can ultimately shorten their lifespan.

Patient falls typically occur in one of two ways, through the result of external environmental (extrinsic) factors or through pathophysiological (intrinsic) factors. Some examples of environmental factors which may lead to a patient fall include, poorly placed furniture, clothing snags on furniture or medical components, wheel chairs with wheels that do not lock or are not locked before a patient attempts to sit down, slippery footwear, overly waxed floors, electrical cords, and long intravenous tubing curled on the floor. Pathophysiological falls, on the other hand, occur when a patient has a decreased level of adaptation to an internal condition, such as, for example, lower extremity weakness, impaired balance, poor vision as well as abnormal gait and mobility. While some pathophysiological falls have a level of predictability, other pathophysiological falls are non-predictable in nature. Some non-predictable falls include, for instance, drop attacks, cardiac arrhythmias, seizure, transient ischemic attacks (TIAs) or cerebrovascular accidents (CVA), as well as drug reactions and/or side effects. Non-predictive pathophysiological falls, however, only account for a very small percentage of the overall falls typically found at most acute care facilities.

Intrinsic and extrinsic falls can be further dissected into personal risk factors, such as patient characteristics or medical diagnoses, which can be objectively measured to predict a patient's fall potential or degree of risk for falling. Because falls are most often the result of more than one interrelated cause, identifying the risk factors involved may prevent a fall from occurring. Moreover, once the risk factors are successfully identified, implementing procedures to reduce, stabilize or even prevent a fall from occurring may be possible. More particularly, if a caregiver understands the degree to which a patient and/or group of patients exhibit a falling risk, the caregiver can develop and/or match an intervention program for these patients to thereby reduce the risk that a fall will happen. As such, there is a desire for developing a method and system for accurately identifying high-risk fall patients so that a care facility's resources can be focused on those patients to thereby prevent such falls from happening.

SUMMARY OF THE INVENTION

According to one exemplary embodiment of the present invention, a method and system for identifying patients who are at risk for falls is provided. In particular, an improved predictive model that is practical for complex hospital environments, easy to add to a basic nursing assessment, and statistically accurate in predicting patient falls, is provided.

In another exemplary embodiment according to the present invention, a method for determining the fall risk of a patient is provided. In particular, a patient is evaluated to determine whether the patient exhibits one or more intrinsic fall risk factors selected from the group consisting of confusion, depression, altered elimination, dizziness, male gender, antiepileptic/anticonvulsant prescriptions and benzodiazepine prescriptions. A point value from a predefined point value range is assigned to each intrinsic risk factor found to be exhibited by the patient. A mobility test is performed on the patient to evaluate the patient's ability to rise from a seated position. A mobility test point value from a predefined point value range is assigned to the patient based upon the patient's performance of the mobility test. The intrinsic risk factor point values are summed together with the mobility test point value to achieve a total risk score, and the patient's fall risk is determined based on the total risk score.

In still another exemplary embodiment, a system for assessing a patient's fall risk is provided. According to this embodiment, the system comprises a means for associating a risk model tool with a computer system, wherein the risk model tool includes a means for evaluating the patient's fall risk score by determining whether a patient exhibits one or more intrinsic fall risk factors selected from the group consisting of confusion, depression, altered elimination, dizziness, male gender, antiepileptic/anticonvulsant prescriptions, benzodiazepine prescriptions and mobility. The patient's fall risk score is input into the computer system, and the patient's fall risk score is stored into an electronic database.

In yet another exemplary embodiment, a method for determining an intervention process for a patient based on a fall risk score is provided. According to this embodiment, the patient is evaluated to determine whether the patient exhibits one or more intrinsic fall risk factors selected from the group consisting of confusion, depression, altered elimination, dizziness, male gender, antiepileptic/anticonvulsant prescriptions and benzodiazepine prescriptions. A point value from a predefined point value range is assigned to each intrinsic risk factor found to be exhibited by the patient. A mobility test is performed on the patient to evaluate the patient's ability to rise from a seated position. A mobility test point value from a predefined point value range is assigned to the patient based upon the patient's performance of the mobility test. The intrinsic risk factor point values are summed together with the mobility test point value to achieve a total risk score. The patient's fall risk is determined based on the total risk score, and an intervention process to perform on the patient based on the patient's fall risk score is created.

These and additional aspects of the present invention will become apparent to those skilled in the art from the following detailed description, which is simply, by way of illustration, various modes contemplated for carrying out the invention. As will be realized, the invention is capable of other different obvious aspects all without departing from the invention. Accordingly, the drawings and specification are illustrative in nature and not restrictive.

BRIEF DESCRIPTION OF THE DRAWINGS

While the specification concludes with claims particularly pointing out and distinctly claiming the present invention, it is believed that the same will be understood from the following description taken in conjunction with the accompanying drawings in which:

FIG. 1 is a representative fall risk factor model used in the fall risk factor patient assessment process according to an exemplary embodiment of the method and system of the present invention;

FIG. 2 is another representative fall risk factor model tool used in the fall risk factor patient assessment process according to an exemplary embodiment of the method and system of the present invention;

FIG. 6 is representative computer operated fall risk factor model tool used in the fall risk factor patient assessment process according to an exemplary embodiment of the method and system of the present invention.

DETAILED DESCRIPTION

Figure 3:
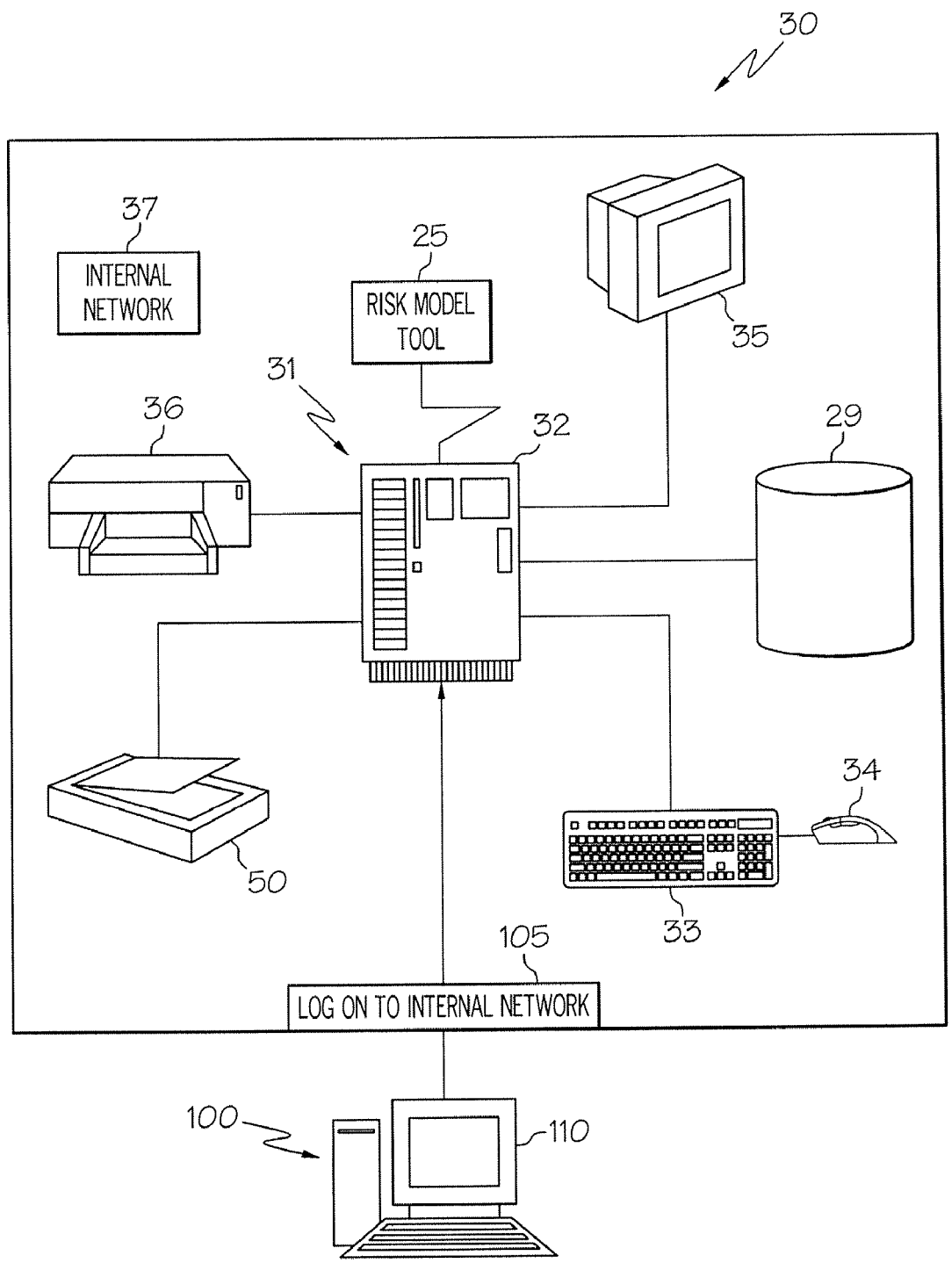
FIG. 3 is a schematic diagram depicting a system constructed and arranged for utilizing the fall risk factor patient assessment process in accordance with an exemplary embodiment of the present invention.

The present invention provides data collection models and assessment methods and tools for collecting and analyzing patient data, particularly data pertaining to patient fall risk factors. As used herein, a "fall" is generally defined as an unanticipated change in body position in a downward motion that may or may not result in a physical injury. Moreover, a fall may occur at any time during the hospitalization process, throughout an outpatient procedure and/or testing procedure or within long-term treatment periods.

In accordance with the present invention, intrinsic fall risk factors of a patient are analyzed to determine the patient's total level of fall risk. This analysis is completed by analyzing the patient according to a series of fall risk factor categories outlined on a fall risk model and completing a fall risk analysis tool based upon an established fall risk point system process. Examples of such predictive fall risk models are generally discussed, for instance in Hendrich et al., "Hospital Falls: Development of a Predictive Model for Clinical Practice," *Applied Nursing Research*, vol. 8, no. 3, (August 1995), pp. 129-139, and Hendrich et al, "Validation of the Hendrich II Fall Risk Model: A Large Concurrent Case/Control Study of Hospitalized Patients," *Applied Nursing Research*, vol. 16, no. 1, (February 2003), pp. 9-21, both of which are herein incorporated by reference in their entirety.

The intrinsic fall risk factors of the present invention are categorized into eight distinct groups. These groups are as follows: 1) confusion, disorientation and/or impulsivity; 2) depression; 3) altered elimination (e.g., problems with control over urinary or bowel elimination); 4) dizziness and/or vertigo; 5) gender; 6) any anticonvulsant and/or antiepileptic prescriptions; 7) any benzodiazepine prescriptions; and 8) a mobility test (e.g., the "get up and go" or "rising from chair" test).

As used herein, confusion, disorientation and/or impulsivity are generally understood to be caused by a vast array of factors and may cause a patient to exhibit varying degrees of impulsive behaviors, such as hallucinations, agitation and/or acting unrealistically, inappropriately or unusual. Moreover, these patients may also not be alert and oriented to person, place and/or time. Confusion, disorientation and/or impulsivity may be caused by factors, such as drug side effects, dementia, metabolic changes, infection, sepsis, fever, and/or psychiatric conditions.

As used herein, patients having depression generally exhibit varying degrees of symptomatic behaviors, such as feelings of helplessness, hopelessness, overwhelming feelings, tearfulness, flat affects or disinterested behavior. Moreover, it should be understood that depression can be admission-related, situational and acute, or chronic in nature.

As used herein, altered elimination issues generally involve patients with conditions such as impaired urinary elimination (incontinence, urgency, nocturia, hesitancy, frequency, dysuria, retention), the inability to reach a toilet in time to avoid unintentional loss of urine, the involuntary passage of urine, and change in normal bowel habits characterized by involuntary passage of stools.

As used herein, dizziness and vertigo are generally understood to involve the sensation a room or surrounding environment is uncontrollably spinning about a patient or individual. This sensation may be brought on by many factors such as medication side-effects, inner ear conditions, CNS impairments, head injuries, infections, metabolic changes, anemia, or a generalized weakness secondary to a disease state. Moreover, secondary causes of these conditions can include dehydration and orthostatic vital sign changes.

With respect to fall risk factors involving medications, it should be understood that the terms "anticonvulsant", "antiepileptic" and "benzodiazepine" are used as general classifications or categories and include all drugs that are related to those categories, even if not specifically mentioned herein.

As used herein, the mobility test (e.g., the "get up and go" or "rising from chair" test) is an intrinsic fall risk factor, which involves a separate testing analysis of a patient and determines if the patient is able to rise from a sitting position without the assistance of an external source. Details of the mobility test will be explained in more detail below.

Referring now to FIG. 1, an exemplary embodiment of the present invention is depicted in which the fall risk score of a patient is determined by using a statistical risk factor model and a "risk points" system. According to this embodiment, a fall risk factor model 10 is presented for assessing the total fall risk score of a patient. The risk factor model 10 includes a listing of risk factors 11 and their associated definitions 12, which describe the general patient characteristics associated with each risk factor 11. According to this exemplary embodiment, the risk factors 11 are divided into eight categories, confusion/disorientation/impulsivity 13, symptomatic depression 14, altered elimination 15, dizziness/vertigo 16, gender 17, any prescribed antiepileptic 18, any prescribed benzodiazepine 19, as well as the mobility (get up and go) test 20.

In general, the risk points system of FIG. 1 is designed so that each patient is evaluated for each risk factor 11 and assigned points 21 based on the patient's response to the risk factor as generally defined by each risk factor's definition 12. If the patient is found to fit the definition 12 for any of the independent risk factory categories 13-20, then the assigned points 21 allotted for that risk factor 11, is recorded as a score 22 within the space provided next to each independent risk factor category 13-20. Once a score 22 is recorded for each independent risk factor category 13-20, then the scores 22 are summed together to determine the total fall risk score 24 of each patient. The total fall risk score 24 of the patient can then be recorded into the total score space 24a provided at the bottom of the model. After the total risk score 24 is determined, the patient is assigned to a risk category, which reflects the total score. According to this exemplary embodiment, a patient is classified as a "high risk" if his or her total score is greater than or equal to five. In yet other exemplary embodiments, a patient is classified as a "high risk" if his or her total score is five or greater.

As part of the risk points system of FIG. 1, the caregiver must also perform a separate mobility test 20 to satisfy the mobility component of the risk factor model. As explained in FIG. 1, the mobility test 20 involves a patient sitting in a chair or on the side of a bed with their palms flat on their thighs. The patient is then asked to stand without assistance. The patient is scored according to the guideline key 9 provided on the risk factor model 10. If the patient is unable to perform the test because of unconsciousness, a drug-induced coma, traction, debilitation/atrophy or a bed rest order, then the caregiver is asked to score all other risk factors that can be assessed. If the patient scores a total risk score 24 of five or greater (without the mobility test 20) and can attempt to get up, they should be considered "high risk for falls".

With respect to the points 21 to be assigned to the patient as part of the risk factor model, the point totals to be assigned to the patient for each independent risk factor category 13-20 are included in Table 1 below.

TABLE 1

| Risk Factor | Points |
|---|---|
| Confusion Disorientation Impulsivity | 4 |
| Symptomatic Depression | 2 |
| Altered Elimination | 1 |
| Dizziness Vertigo | 1 |
| Gender | 1 |
| Any Prescribed Antiepileptics | 2 |
| Any Prescribed Benzodiazepines | 1 |
| Mobility/Get Up & Go Test | |
| Ability to rise in a single movement | 0 |
| Pushes up, successful in one attempt | 1 |
| Multiple attempts, but successful | 3 |
| Unable to rise without assistance during test (OR if a medical order states the same and/or complete bed rest is ordered) | 4 |

In another exemplary embodiment according to the present invention, a risk assessment tool for implementing a fall risk model of a patient is utilized, for example, in a clinical or acute care setting. According to this embodiment, a nurse or other healthcare provider uses a risk model tool 25 such as is shown in FIG. 2 during normal patient care procedures. The nurse or other healthcare provider uses the tool 25 to evaluate the patient to determine if the patient exhibits any of the indicated intrinsic risk factors 26. According to this exemplary embodiment, the nurse or other healthcare provider can determine the patient's intrinsic risk factors 26, for example, by physically observing the patient and/or reviewing the patient's medical record. If an intrinsic risk factor 26 is determined to be present after the patient is evaluated, then a point total 27 can be recorded on the tool 25 by the nurse or other healthcare provider in each of the intrinsic risk factor 26 categories, and specifically in an amount equal to the allotted point total included next to each risk factory category.

All of the point totals 27 awarded in each of the intrinsic risk factor 26 categories are then summed together to determine the patient's total risk score 28. The total risk score 28 can then serve as a measure of the patient's level of risk of falling. In this illustrated exemplary embodiment, a higher total risk score 28 corresponds to a higher level of risk.

Those skilled in the art will understand that the tool 25 of FIG. 2 and the risk factor model 10 of FIG. 1 may be utilized in any medium which is recordable, for instance, paper form, electronic form and/or audiovisual recordable form. As one example, the tools may be implemented using an electronic computing device such as desktop computer, laptop, PDA (personal digital assistant), cell phone having computing capabilities, handheld device, or other portable or stationary computing device.

In the embodiment where a paper form is used, each patient's risk information is initially handwritten on the form. The data may then be input and stored in one or more files or databases on a stationary or portable computer. Alternatively or in addition, the completed paper forms may be converted to digital form (e.g., by scanning to create digital images of the forms) and stored in a computer.

In embodiments where an electronic form is used, each patient's risk information may be entered by a caregiver and stored within an electronic database as desired. An exemplary illustration of an electronic form according to the present invention is depicted within FIG. 6. It should be understood that this form may be used in conjunction with a computer system as explained in detail below.

In another exemplary embodiment, as generally depicted by FIG. 3, a risk model tool 25 is implemented into an electronic database 29 through the assistance of a computer system 30. According to this illustrated embodiment, computer system 30 includes at least one user interface 31, which utilizes computer programming logic to operate a stationary or portable computing device 32. The computing device 32 has conventional input devices, such as a keyboard 33, and a mouse 34, a conventional electronic display screen 35 (such as a monitor, LCD screen, or other suitable display), and optionally a conventional hardcopy output device 36 (e.g., a laser printer). Those skilled in the art will appreciate that other suitable input devices may also be utilized according to this embodiment, including but not limited to, an electronic stylus or a voice recognition system.

While not required, the computer system of FIG. 3 may be configured to operate via an accessible computer network 37 (depicted as an internal network in this exemplary embodiment). Common examples of such a network are an internal Intranet and/or external Internet system. It should be understood that data can be provided for analysis and storage either via Internet/Intranet transmission or email, portable computer storage device or diskette, or by direct entry.

In another exemplary embodiment according to this illustration, a second user interface 100 may be established outside the network 37. According to this embodiment, an outside user can access the computing device 32 by logging on to the network 105 through the assistance of an outside computing device 110 located at a remote location. It should be understood that the outside user can access the network 37 through the assistance of a modem (not shown) and/or a commercial internet service provider or other similar means. Once the outside user attempts to log onto the network 37 by accessing the network's appropriate website or IP address, a system can be established such that a dialog box is activated prompting the user to enter a recognized username and password. Once the appropriate username and password is entered, the user can then enter the internal network's computer system and electronic database.

While not discussing this process in detail herein, those skilled in the relevant art will appreciate that the outside user can perform all or some of the processes found on the network 37 depending on how the computer privileges are set up. More particularly, it should be understood that the level of computer access and permissions granted to the outside user can be specifically defined by the administrator of the computer system.

Still referring to FIG. 3, a user can input the risk points of a patient into the computer system 30 at the user interface 31 through the assistance of the input devices 33 and 34. Depending on how the computer system is arranged, the computer programming logic may be configured to automatically calculate the patient's total risk score 28, or instead be manually entered at the direction of the user. As such, the total risk score 28 may be configured to automatically calculate and update itself each time the risk points are entered to thereby give a running total, or, alternatively, after all the risk points have been entered. Once the risk point data for the patient is entered, the data is stored within the system's electronic database 29, which may be a physical storage device, spreadsheet, or the like.

In some exemplary embodiments according to this illustration, a server operating under the control of one or more computer software programs may be utilized to carry out the steps indicated above. Furthermore, according to this exemplary embodiment, the server may be electronically coupled to a network and computer storage device, such that the server is in communication with at least one user interface having conventional input devices as described above. The user interface may also be connected to a data input device capable of automated paper form reading, such as a scanner 50 as depicted in FIG. 3.

Although not indicated in the drawings, it should be understood that the computer system 30 may be implemented by other known methods of computer networking and that the arrangement of component devices is not restricted to that which is described herein. It should be further understood that the computer system 30 can be composed of alternative devices having similar functions to the component devices described herein and may alternatively operate through the assistance of one or more established software programs.

Figure 4:
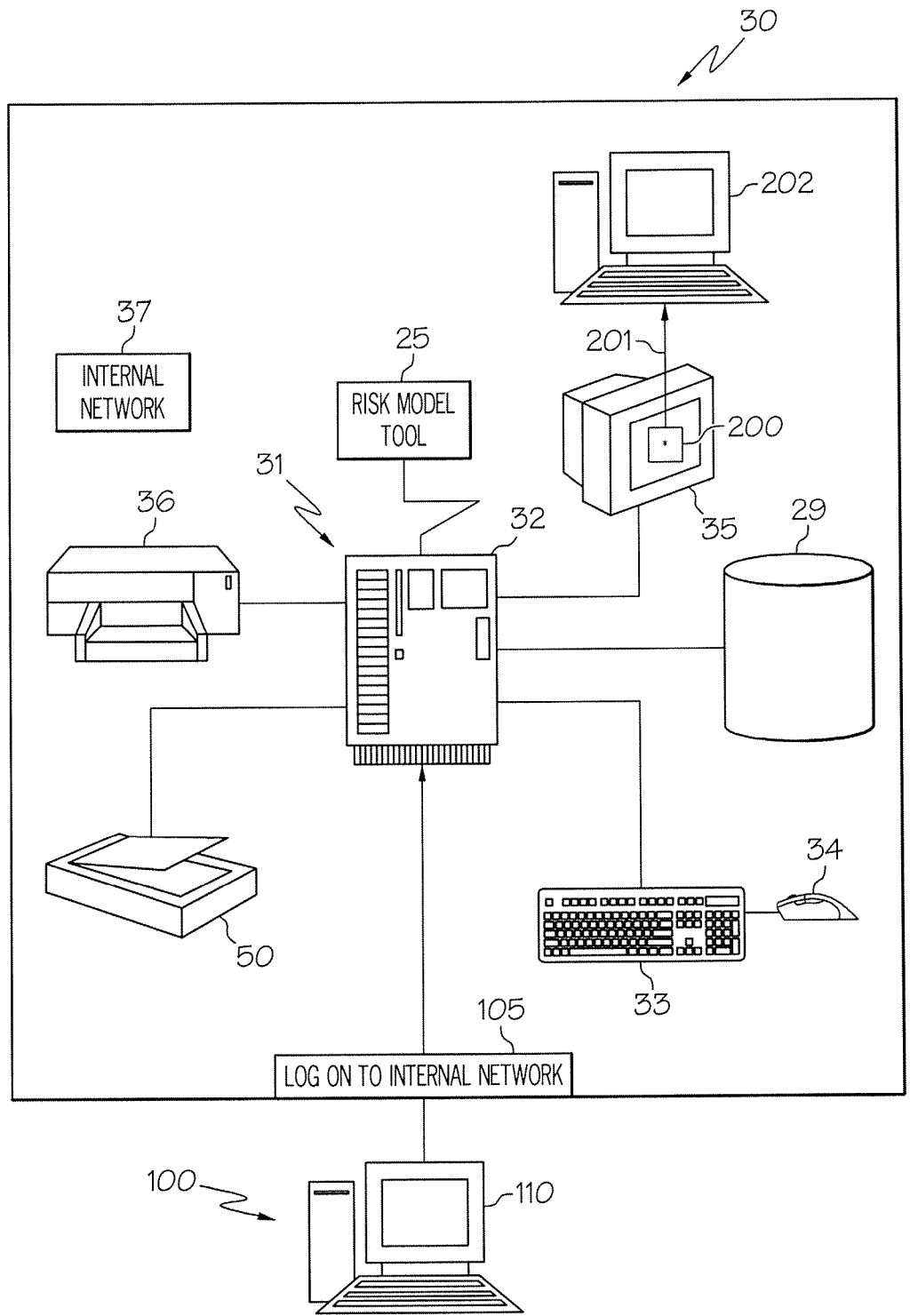
FIG. 4 is another schematic diagram depicting a system constructed and arranged for utilizing the fall risk factor patient assessment process in accordance with an exemplary embodiment of the present invention.

As depicted by FIG. 4, once the total risk score 28 of a patient has been determined, a message or alert 200 can be generated if the patient is at a high risk of falling. For example, when the patient has a high total risk score, a message or alert 200 may be automatically displayed on the electronic display screen 35 of the user interface 31 so that the user is aware that the patient is at a high risk of a fall. The message or alert 200 may be delivered in any known form, such as a text message, a flashing LED light, audible sound, or the like. Moreover, an appropriate message or alert 200 may also be generated based on the patient's total score, regardless of whether the patient is a high fall risk or not. In either case, the alert or message 200 may be structured so that it automatically transmits an electronic communication 201, such as an instant message or electronic mail message, to a remote computing station 202 or similar computing device. Such a transmission may accomplished by electronic or wireless networks or other suitable means.

The remote computing station 202 may be located at a nursing station, or may be alternatively connected directly to the caregiver, such as via a pager, cell phone, PDA, or other computing device. According to this exemplary embodiment, once the electronic communication 201 is received by the appropriate caregiver, they may in turn go conduct an intervention with the patient so that the fall risk associated with the patient is minimized or eliminated.

It should be understood that a patient's fall risk data may be stored in temporary or permanent computer memory (e.g., volatile or nonvolatile memory). In one exemplary embodiment, the patient's risk scores for all risk factors, as well as the total risk score 28, are stored in the electronic database 29 of the computer system 30 for further review and/or analysis. In another embodiment, only the patient's total risk score 28 is stored in the electronic database 29.

Figure 5:
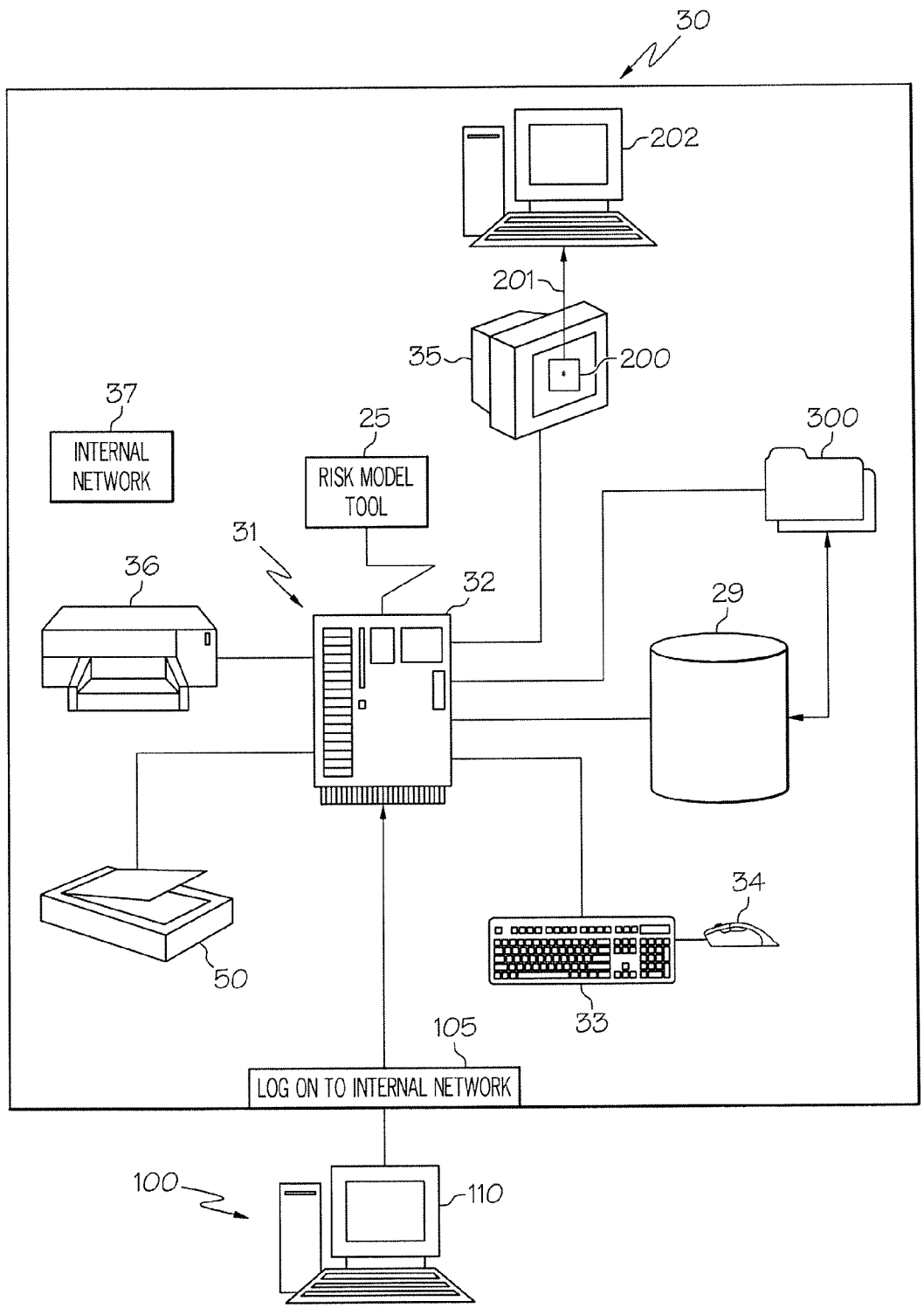
FIG. 5 is another schematic diagram depicting a system constructed and arranged for utilizing the fall risk factor patient assessment process in accordance with an exemplary embodiment of the present invention.

In certain exemplary embodiments, as depicted by FIG. 5, a patient's medical records 300 may be associated with the computer system and its database 29 so that the records 300 may be updated with the fall risk data. The updating of the patient's medical records 300 may be done automatically or at the manual request of a user at the user interface 31. In this way, the fall risk data is made available to all doctors, nurses, and other healthcare providers who have access to the patient's medical records.

In a further exemplary embodiment, a patient may be accessed for their total risk score 28 several times over a given period of time. According to this embodiment, risk data for each instance of risk evaluation may be stored in the electronic database 29 of the computer system 30, and computer programming logic may be used to compare the risk data over time to determine trends of increasing or decreasing risk. For example, trends may be displayed graphically in the form of a line graph. In addition, a system may be established, as explained above, such that a healthcare provider is automatically notified of a trend or changes in a trend, by an alert or message 200 so that they may intervene with the patient accordingly.

In another exemplary embodiment, the total risk scores for multiple patients may be associated with the computer system 30 so that each patient's fall risk data may be stored in the electronic database 29 for comparison and analysis. For example, the risk scores (individual or aggregate) of patients in different wings, rooms, or departments of a hospital may be compared to identify other factors that may be contributing to increased or decreased fall risk.

In yet another embodiment, computer programming logic is used to provide the healthcare provider with information and/or suggestions for changing a patient's treatment or therapy based on the patient's risk score or scores over time. Such information and/or suggestions are communicated to the healthcare provider by any of the communication means discussed above, or other suitable means known in the art.

Once a total risk score has been determined for a patient according to the methods described above, the nurse or other healthcare provider may then initiate an appropriate intervention (e.g., treatment or therapy recommendation) session for the patient, or take other actions, based on the patient's total risk score. It should be understood that an intervention session should be conducted by a caregiver based upon their clinical judgment skills together with a balancing of the scientific knowledge readily available within the relevant medical field.

To illustrate how the intervention process operates according to exemplary embodiments of the present invention, assume a patient has been analyzed for their total risk factor score as explained above. After this process, it is determined that the patient has a total risk factor score of greater than or equal to five, and is thereby at a high risk of falling. With this score now calculated, the caregiver is able to select an appropriate intervention process for this patient by referencing Table 2 shown in the Appendix, which is incorporated herein by this reference. For example, if the patient exhibits signs of confusion and incontinence, the caregiver would need to determine the cause and duration of the confusion and whether it is acute or chronic (dementia) in nature. If the confusion is determined to be acute in nature, the caregiver must determine the underlying cause, which necessitates supervised elimination and frequent assessment of elimination needs.

To continue the above example, and referring to Table 2 in the Appendix, this patient may be a prime candidate for a bed exit feature and gait training to reduce the presence of their specific risk factors. Putting this patient in restraints or keeping them in bed, for instance, may increase confusion and immobility.

While not required, it is recommended that a caregiver reassess their patients according to the method and system of the present invention each shift and/or at least when a patient's condition changes. This reassessment should be performed even if the patient was not shown to be at a high risk for a fall, as patient conditions can fluctuate greatly throughout their hospital stay. Interventions to prevent falls should be matched against the risk factors. The caregiver should use his or her clinical judgment to determine the intervention that is most appropriate. Once a determination has been made, it is recommended that the caregiver document the interventions on the patient's medical record. Moreover, the caregiver should also make sure that the interventions are implemented consistently throughout the shift.

After a patient is assessed for a risk factor as explained above, five additional elements are useful for performing the intervention process according to the method and system of the present invention (See Table 2 in the Appendix). These elements include: 1) safe environment; 2) elimination needs; 3) monitoring/observing activities and mobility; 4) patient/family education; and 5) team management.

Safe Environment

A safe environment is a crucial part of an effective fall prevention program. Knowing about the extrinsic causes of falls and being aware of them will help the caregiver make the patient's environment safe.

Elimination Needs

The number one cause of falls in a high-risk patient is related to their elimination needs (i.e., the patient tries to make it to the bathroom without external assistance). According to this category, the following areas are all related to altered elimination issues: impaired urinary elimination; toileting self-care deficiencies; functional urinary incontinence; reflex urinary incontinence; stress urinary incontinence; total urinary incontinence; and urge urinary incontinence.

It is recommended to implement scheduled toileting sessions, which are matched against the patient's needs and/or about two hours after meals.

Monitor/Observe Activities/Mobility

Patients often fall when they are trying to perform daily activities or move about. As such, monitoring a patient's activities and assessing their mobility skills is a crucial part of implementing an effective fall prevention program.

Patient/Family Education

Caregivers often take for granted that a patient is knowledgeable about his or her condition and how it affects their normal functional abilities. Moreover, the teamwork necessary for preventing falls has to include family and significant others as a part of the team. Therefore, educating the patient and his or her family about the patient's condition, as well as their activity and mobility skills is another crucial part of a successful fall prevention program.

Team Management (Interdisciplinary Patient Management

Preventing falls requires teamwork, which is an interdisciplinary approach. Every person in the healthcare system needs to take a proactive approach. Working as a team to identify the risk factors, assessing the patient, and acting upon these findings are all imperative. Everyone has an equally important role to play in falls prevention.

Advantages and improvements of the systems and methods of the present invention are demonstrated in the above-described examples. The examples are illustrative only and are not intended to limit or preclude other embodiments of the invention.

Although the invention has been described in detail with reference to certain exemplary embodiments, it will be understood by one of ordinary skill in the art that variations and modifications exist and fall within the scope and spirit of the present invention.

APPENDIX - TABLE 2

Intervention Processes

I. Confusion

1. Assess the patient for confusion

Approach the patient consistently and appropriately: consistent caregivers, kind firmness, active friendliness, passive friendliness, calm and unhurried, matter-of-fact, and no demands
Orient patient to person, place,
Provide a consistent, recognizable, low-stimulating physical environment and daily routine. Prepare patient for upcoming changes in usual routine and environment
Monitor for changes in sensation and orientation, including presence of content that is violent or self-harmful, changes in muscle strength, peripheral numbness . . .
Monitor for changes and outliers in lab values which can cause abnormal neurological manifestations such as altered sensorium and weakness. This includes: acid-base, fluid and electrolyte, blood glucose, arterial pH level, PaCO2, HCO3, hyper and hypokalemia, hyper and hyponatremia, hyper and hypocalcemia, magnesium and phosphate levels.
Monitor and provide appropriate nursing interventions for fluctuations and abnormalities in vital signs: pain, fever, oxygen levels.

2. Safe Environment identify individual safety needs of the patient
remove harmful hazards (e.g. loose rugs, small, moveable furniture, tubing, electrical cords)
safeguard with side rails/side rail padding as appropriate, low-height bed, firm mattress
place frequently used objects within reach: call light, bed positioning switch,
block the patient's view of the bathroom, commode or other equipment used for elimination
provide appropriate level (and least restrictive) of supervision/surveillance to monitor patient and to allow for therapeutic actions, as needed
initiate and maintain precaution status for patient at high risk for dangers specific to the are setting
communicate information about patient's risk to other nursing staff
Escort patient to off-ward activities as appropriate 3. Elimination Needs Avoid the "I'll be right back" syndrome, and leaving patient on a toilet or commode
Provide appropriate peri and anal care. Assist patient in accomplishing appropriate post-elimination hygiene.
Remove essential clothing to allow for elimination
Instruct patient to respond immediately to urge to void, as appropriate

APPENDIX - TABLE 2-continued

Intervention Processes

Instruct patient to empty bladder prior to activity, relevant procedures
Provide enough time for bladder emptying (10 minutes). Monitor for possible urine retention using a bladder scanner or other appropriate means

4. Monitor/Observe Activities/Mobility

Perform gait assessment: "Get Up and Go Test" to determine how much assistance is required. Consider a physical therapy consult if very unsteady.
Collaborate with the physician to minimize "bedrest" orders. Bedrest promotes deconditioning in all age groups.
Medicate prior to an activity to increase participation, but evaluate the hazard of sedation
Provide self-care assistance. Encourage independence but intervene when patient is unable to perform
Provide appropriate adaptive mobility devices
monitor patient's need for adaptive deices for personal hygiene, dressing, grooming, toileting and eating & provide assistance until patient is fully able to assume self-care
Provide adequate rest periods

5. Patient/Family Education

Encourage family to stay with patient, as appropriate
Consult with family to establish patient's pre-injury cognitive baseline
Inform family members of factors that may improve patient's condition
Include family/SO in planning, providing and evaluating care to the extent desired
Teach family about prescribed activity, safety, medication, dietary, elimination and self-care parameters

6. Team Management

Collaborate with team to monitor therapeutic effects of the medication
Collaborate with team to monitor for signs and symptoms of drug toxicity, as well as adverse effects of the drug
Monitor serum blood levels (e.g. electrolytes, prothrombin, medications) as appropriate
Collaborate with team members to find the most appropriate activity level for the patient
Collaborate with team members to find the most beneficial diet plan for the patient

Depression

1. Assess the Patient for Depression

Indicators of depression include: depressed mood, loss of interest in activities, negative life events, lack of pleasure in activities, impaired concentration, inappropriate guilt, excessive guilt, fatigue, feelings of worthlessness, psychomotor retardation, psychomotor agitation, insomnia, hypersomnia, weight gain, weight loss, increased appetite, decreased appetite, recurrent thoughts of suicide or death, indecisiveness, sadness, crying spells, anger, hopelessness, loneliness, low self-esteem, decreased activity level, poor personal hygiene/grooming Monitor for changes in sensation and orientation, including presence of content that is violent or self-harmful, changes in muscle strength, peripheral numbness . . .
Monitor for changes and outliers in lab values which can cause abnormal neurological manifestations such as altered sensorium and weakness. This includes: acid-base, fluid and electrolyte, blood glucose, arterial pH level, PaCO2, HCO3, hyper and hypokalemia, hyper and hyponatremia, hyper and hypocalcemia, magnesium and phosphate levels.
Monitor and provide appropriate nursing interventions for fluctuations and abnormalities in vital signs: pain, fever, oxygen levels.

2. Safe Environment identify individual safety needs of the patient
remove harmful hazards (e.g. loose rugs, small, moveable furniture, tubing, electrical cords)
safeguard with side rails/side rail padding as appropriate, low-height bed, firm mattress
place frequently used objects within reach: call light, bed positioning switch,
block the patient's view of the bathroom, commode or other equipment used for elimination
provide appropriate level (and least restrictive) of supervision/surveillance to monitor patient and to allow for therapeutic actions, as needed
initiate and maintain precaution status for patient at high risk for dangers specific to the are setting
communicate information about patient's risk to other nursing staff
Escort patient to off-ward activities as appropriate

3. Elimination Needs

Assess patient's need for toileting every two hours. Assist patient to toilet/commode/bedpan/fracture pan/urinal at specified intervals
Avoid the "I'll be right back" syndrome, and leaving patient on a toilet or commode
Provide appropriate peri and anal care. Assist patient in accomplishing appropriate post-elimination hygiene.
Remove essential clothing to allow for elimination
Instruct patient to respond immediately to urge to void, as appropriate
Instruct patient to empty bladder prior to activity, relevant procedures
Provide enough time for bladder emptying (10 minutes). Monitor for possible urine retention using a bladder scanner or other appropriate means

4. Monitor/Observe Activities/Mobility

Perform gait assessment: "Get Up and Go Test" to determine how much assistance is required. Consider a physical therapy consult if very unsteady.
Collaborate with the physician to minimize "bedrest" orders. Bedrest promotes deconditioning in all age groups.
Medicate prior to an activity to increase participation, but evaluate the hazard of sedation
Provide self-care assistance. Encourage independence but intervene when patient is unable to perform
Provide appropriate adaptive mobility devices
monitor patient's need for adaptive deices for personal hygiene, dressing, grooming, toileting and eating & provide assistance until patient is fully able to assume self-care
Provide adequate rest periods

5. Patient/Family Education

Encourage family to stay with patient, as appropriate
Consult with family to establish patient's pre-injury cognitive baseline
Inform family members of factors that may improve patient's condition
Include family/SO in planning, providing and evaluating care to the extent desired
Teach family about prescribed activity, safety, medication, dietary, elimination and self-care parameters

6. Team Management

Collaborate with team to monitor therapeutic effects of the medication
Collaborate with team to monitor for signs and symptoms of drug toxicity, as well as adverse effects of the drug
Monitor serum blood levels (e.g. electrolytes, prothrombin, medications) as appropriate
Collaborate with team members to find the most appropriate activity level for the patient
Collaborate with team members to find the most beneficial diet plan for the patient

Dizziness/Vertigo

1. Assess the Patient for Dizziness/Vertigo

Evaluate sensory functions (e.g., vision, hearing and proprioception)
Monitor patient's emotional, cardiovascular and functional responses to exercise and position change
Monitor for changes in sensation and orientation, including APPENDIX - TABLE 2-continued Intervention Processes presence of content that is violent or self-harmful, changes in muscle strength, peripheral numbness . . .
Monitor for changes and outliers in lab values which can cause abnormal neurological manifestations such as altered sensorium and weakness. This includes: acid-base, fluid and electrolyte, blood glucose, arterial pH level, PaCO2, HCO3, hyper and hypokalemia, hyper and hyponatremia, hyper and hypocalcemia, magnesium and phosphate levels.
Monitor and provide appropriate nursing interventions for fluctuations and abnormalities in vital signs: pain, fever, oxygen levels.
2. Safe Environment identify individual safety needs of the patient
remove harmful hazards (e.g. loose rugs, small, moveable furniture, tubing, electrical cords)
safeguard with side rails/side rail padding as appropriate, low-height bed, firm mattress
place frequently used objects within reach: call light, bed positioning switch,
block the patient's view of the bathroom, commode or other equipment used for elimination
provide appropriate level (and least restrictive) of supervision/surveillance to monitor patient and to allow for therapeutic actions, as needed
initiate and maintain precaution status for patient at high risk for dangers specific to the are setting
communicate information about patient's risk to other nursing staff
Escort patient to off-ward activities as appropriate
3. Elimination Needs Assess patient's need for toileting every two hours. Assist patient to toilet/commode/bedpan/fracture pan/urinal at specified intervals
Avoid the "I'll be right back" syndrome, and leaving patient on a toilet or commode
Provide appropriate peri and anal care. Assist patient in accomplishing appropriate post-elimination hygiene.
Remove essential clothing to allow for elimination
Instruct patient to respond immediately to urge to void, as appropriate
Instruct patient to empty bladder prior to activity, relevant procedures
Provide enough time for bladder emptying (10 minutes). Monitor for possible urine retention using a bladder scanner or other appropriate means
4. Monitor/Observe Activities/Mobility Perform gait assessment: "Get Up and Go Test" to determine how much assistance is required. Consider a physical therapy consult if very unsteady.
Collaborate with the physician to minimize "bedrest" orders. Bedrest promotes deconditioning in all age groups.
Medicate prior to an activity to increase participation, but evaluate the hazard of sedation
Provide self-care assistance. Encourage independence but intervene when patient is unable to perform
Provide appropriate adaptive mobility devices
Monitor patient's need for adaptive deices for personal hygiene, dressing, grooming, toileting and eating & provide assistance until patient is fully able to assume self-care
Provide adequate rest periods
exercise therapy: ambulation, joint mobility, balance, muscle control,
position to alleviate dyspnea (e.g., semi-Fowler's, "good lung down") as appropriate
provide support to edematous areas as appropriate
5. Patient/Family Education instruct patient on structure and function of spine and optimal posture for moving and using the body
instruct patient about need for correct posture to prevent fatigue, strain or injury
instruct in availability and usage of assistive devices, if appropriate instruct patient/caregiver about safe transfer and ambulation techniques
Encourage family to stay with patient, as appropriate
Consult with family to establish patient's pre-injury cognitive baseline
Inform family members of factors that may improve patient's condition
Include family/SO in planning, providing and evaluating care to the extent desired
Teach family about prescribed activity, safety, medication, dietary, elimination and self-care parameters
6. Team Management Collaborate with PT, OT and recreational therapies in developing and executing a mobility and activity program
Collaborate with team to monitor therapeutic effects of the medication
Collaborate with team to monitor for signs and symptoms of drug toxicity, as well as adverse effects of the drug
Monitor serum blood levels (e.g. electrolytes, prothrombin, medications) as appropriate
Collaborate with team members to find the most beneficial diet plan for the patient Male 1. Assess the Patient Appropriately Monitor for changes in sensation and orientation, including presence of content that is violent or self-harmful, changes in muscle strength, peripheral numbness . . .
Monitor for changes and outliers in lab values which can cause abnormal neurological manifestations such as altered sensorium and weakness. This includes: acid-base, fluid and electrolyte, blood glucose, arterial pH level, PaCO2, HCO3, hyper and hypokalemia, hyper and hyponatremia, hyper and hypocalcemia, magnesium and phosphate levels.
Monitor and provide appropriate nursing interventions for fluctuations and abnormalities in vital signs: pain, fever, oxygen levels.
2. Safe Environment identify individual safety needs of the patient
remove harmful hazards (e.g. loose rugs, small, moveable furniture, tubing, electrical cords)
safeguard with side rails/side rail padding as appropriate, low-height bed, firm mattress
place frequently used objects within reach: call light, bed positioning switch,
block the patient's view of the bathroom, commode or other equipment used for elimination
provide appropriate level (and least restrictive) of supervision/surveillance to monitor patient and to allow for therapeutic actions, as needed
initiate and maintain precaution status for patient at high risk for dangers specific to the are setting
communicate information about patient's risk to other nursing staff
Escort patient to off-ward activities as appropriate
3. Elimination Needs Assess patient's need for toileting every two hours. Assist patient to toilet/commode/bedpan/fracture pan/urinal at specified intervals
Avoid the "I'll be right back" syndrome, and leaving patient on a toilet or commode
Provide appropriate peri and anal care. Assist patient in accomplishing appropriate post-elimination hygiene.
Remove essential clothing to allow for elimination
Instruct patient to respond immediately to urge to void, as appropriate
Instruct patient to empty bladder prior to activity, relevant procedures
Provide enough time for bladder emptying (10 minutes). Monitor for possible urine retention using a bladder scanner or other appropriate means

APPENDIX - TABLE 2-continued

Intervention Processes

4. Monitor/Observe Activities/Mobility

Perform gait assessment: "Get Up and Go Test" to determine how much assistance is required. Consider a physical therapy consult if very unsteady.
Collaborate with the physician to minimize "bedrest" orders. Bedrest promotes deconditioning in all age groups.
Provide self-care assistance. Encourage independence but intervene when patient is unable to perform
Provide appropriate adaptive mobility devices
monitor patient's need for adaptive deices for personal hygiene, dressing, grooming, toileting and eating & provide assistance until patient is fully able to assume self-care
Provide adequate rest periods

5. Patient/Family Education

Encourage family to stay with patient, as appropriate
Consult with family to establish patient's pre-injury cognitive baseline
Inform family members of factors that may improve patient's condition
Include family/SO in planning, providing and evaluating care to the extent desired
Teach family about prescribed activity, safety, medication, dietary, elimination and self-care parameters

6. Team Management

Collaborate with PT, OT and recreational therapies in developing and executing a mobility and activity program
Collaborate with team to monitor therapeutic effects of the medication
Collaborate with team to monitor for signs and symptoms of drug toxicity, as well as adverse effects of the drug
Monitor serum blood levels (e.g. electrolytes, prothrombin, medications) as appropriate
Collaborate with team members to find the most beneficial diet plan for the patient

Altered Elimination

1. Assess the Patient for Altered Elimination Patterns determine physical or psychological cause of fecal and/or urinary incontinence
monitor bowel movements and bladder habits including frequency, consistency, shape and volume and color as appropriate and report any inconsistencies or irregularities
Monitor for changes in sensation and orientation, including presence of content that is violent or self-harmful, changes in muscle strength, peripheral numbness . . .
Monitor for changes and outliers in lab values which can cause abnormal neurological manifestations such as altered sensorium and weakness.
This includes: acid-base, fluid and electrolyte, blood glucose, arterial pH level, PaCO2, HCO3, hyper and hypokalemia, hyper and hyponatremia, hyper and hypocalcemia, magnesium and phosphate levels.
Monitor and provide appropriate nursing interventions for fluctuations and abnormalities in vital signs: pain, fever, oxygen levels.

2. Safe Environment block the patient's view of the bathroom, commode or other equipment used for elimination
identify individual safety needs of the patient
remove harmful hazards (e.g. loose rugs, small, moveable furniture, tubing, electrical cords)
safeguard with side rails/side rail padding as appropriate, low-height bed, firm mattress
place frequently used objects within reach: call light, bed positioning switch,
block the patient's view of the bathroom, commode or other equipment used for elimination
provide appropriate level (and least restrictive) of supervision/surveillance to monitor patient and to allow for therapeutic actions, as needed
initiate and maintain precaution status for patient at high risk for dangers specific to the are setting
communicate information about patient's risk to other nursing staff
Escort patient to off-ward activities as appropriate

3. Elimination Needs

Assess patient's need for toileting every two hours. Assist patient to toilet/commode/bedpan/fracture pan/urinal at specified intervals
Avoid the "I'll be right back" syndrome, and leaving patient on a toilet or commode
Provide appropriate peri and anal care. Assist patient in accomplishing appropriate post-elimination hygiene.
Remove essential clothing to allow for elimination
Instruct patient to respond immediately to urge to void, as appropriate
Instruct patient to empty bladder prior to activity, relevant procedures
Provide enough time for bladder emptying (10 minutes). Monitor for possible urine retention using a bladder scanner or other appropriate means

4. Monitor/Observe Activities/Mobility

Perform gait assessment: "Get Up and Go Test" to determine how much assistance is required. Consider a physical therapy consult if very unsteady.
Collaborate with the physician to minimize "bedrest" orders. Bedrest promotes deconditioning in all age groups.
Place on incontinent pads and provide incontinent garments as needed
Provide self-care assistance. Encourage independence but intervene when patient is unable to perform
Provide appropriate adaptive mobility devices
Monitor patient's need for adaptive deices for personal hygiene, dressing, grooming, toileting and eating & provide assistance until patient is fully able to assume self-care
Provide adequate rest periods

5. Patient/Family Education

Determine goals of toileting routine and management program with patient/SO
Explain importance of requesting caregiver assistance when toileting
ensure privacy
instruct in availability and usage of assistive devices, if appropriate
instruct patient/caregiver about safe transfer and ambulation techniques
Encourage family to stay with patient, as appropriate
Consult with family to establish patient's pre-injury cognitive baseline
Inform family members of factors that may improve patient's condition
Include family/SO in planning, providing and evaluating care to the extent desired
Teach family about prescribed activity, safety, medication, dietary, elimination and self-care parameters

6. Team Management

Monitor diet and fluid requirements, intake and output
Collaborate with team to monitor therapeutic effects of the medication, especially calcium channel blockers, anticholinergics
Collaborate with team to monitor for signs and symptoms of drug toxicity, as well as adverse effects of the drug
Collaborate with team members to find the most appropriate activity level for the patient

Mobility

1. Assess the Patient for Particular Mobility Needs and/or Deficiencies

Evaluate sensory functions (e.g., vision, hearing and proprioception)
Monitor patient's emotional, cardiovascular and functional responses to exercise and position change
Monitor for changes and outliers in lab values which can cause abnormal neurological manifestations such as altered sensorium and weakness. This includes: acid-base, fluid and electrolyte,

APPENDIX - TABLE 2-continued

Intervention Processes blood glucose, arterial pH level, PaCO2, HCO3, hyper and
hypokalemia, hyper and hyponatremia, hyper and hypocalcemia,
magnesium and phosphate levels.
Monitor and provide appropriate nursing interventions for
fluctuations and abnormalities in vital signs: pain, fever, oxygen
levels.

2. Safe Environment identify individual safety needs of the patient
remove harmful hazards (e.g. loose rugs, small, moveable
furniture, tubing, electrical cords)
safeguard with side rails/side rail padding as appropriate, low-
height bed, firm mattress
place frequently used objects within reach: call light, bed
positioning switch,
block the patient's view of the bathroom, commode or other
equipment used for elimination
provide appropriate level (and least restrictive) of
supervision/surveillance to monitor patient and to allow for
therapeutic actions, as needed
initiate and maintain precaution status for patient at high risk for
dangers specific to the are setting
communicate information about patient's risk to other nursing
staff
Escort patient to off-ward activities as appropriate 3. Elimination Needs Assess patient's need for toileting every two hours. Assist patient
to toilet/commode/bedpan/fracture pan/urinal at specified
intervals
Avoid the "I'll be right back" syndrome, and leaving patient on a
toilet or commode
Provide appropriate peri and anal care. Assist patient in
accomplishing appropriate post-elimination hygiene.
Remove essential clothing to allow for elimination
Instruct patient to respond immediately to urge to void, as
appropriate
Instruct patient to empty bladder prior to activity, relevant
procedures
Provide enough time for bladder emptying (10 minutes). Monitor
for possible urine retention using a bladder scanner or other
appropriate means 4. Monitor/Observe Activities/Mobility Perform gait assessment: "Get Up and Go Test" to determine how
much assistance is required. Consider a physical therapy consult
if very unsteady.
Collaborate with the physician to minimize "bedrest" orders.
Bedrest promotes deconditioning in all age groups.
Medicate prior to an activity to increase participation, but
evaluate the hazard of sedation
Provide self-care assistance. Encourage independence but
intervene when patient is unable to perform
Monitor patient's need for adaptive deices for personal hygiene,
dressing, grooming, toileting and eating & provide assistance
until patient is fully able to assume self-care
Provide exercise therapy: ambulation, joint mobility, balance,
muscle control,
Dress patient in nonrestrictive clothing
Provide assistive devices to support patient in performing
determine patient's ability to participate in activities requiring
balance
Position to alleviate dyspnea (e.g., semi-Fowler's, "good lung
down") as appropriate. Provide adequate rest periods 5. Patient/Family Education instruct patient on structure and function of spine and optimal
posture for moving and using the body
instruct patient about need for correct posture to prevent fatigue,
strain or injury
instruct in availability and usage of assistive devices, if
appropriate
instruct patient/caregiver about safe transfer and ambulation
techniques
Encourage family to stay with patient, as appropriate
Consult with family to establish patient's pre-injury cognitive
baseline
Inform family members of factors that may improve patient's
condition
Include family/SO in planning, providing and evaluating care to
the extent desired
Teach family about prescribed activity, safety, medication,
dietary, elimination and self-care parameters 6. Team Management Collaborate with PT in developing a body mechanics and
ambulation promotion plan as indicated
Collaborate with team to monitor therapeutic effects of the
medication
Collaborate with team to monitor for signs and symptoms of drug
toxicity, as well as adverse effects of the drug
Monitor serum blood levels (e.g. electrolytes, prothrombin,
medications) as appropriate
Collaborate with team members to find the most appropriate
activity level for the patient
Collaborate with team members to find the most beneficial diet
plan for the patient

Anticonvulsants & Antiepileptics & Benzodiazepines

1. Assess

Assess the patient for common side effects of benzodiazepines:
drowsiness, poor concentration, "emotional blunting," ataxia,
dysarthria, motor incoordination, diplopia, muscle weakness,
vertigo and mental confusion. Blurred vision, headache, seizures,
slurred speech, difficulty in depth perception, muscle spasm,
muscle weakness, hypotension, palpitations, tachycardia
Assess the patient for common side effects of anticonvulsants:
muscle weakness, aggressiveness, argumentative behavior,
hyperactivity, agitation, depression, euphoria, irritability,
forgetfulness and confusion, nystagmus, unsteady gait, slurred
speech, dysarthria, vertigo, insomnia, and diplopia, akinesia,
hemiparesis, tremor, hypotonia, headache and choreiform
Evaluate sensory functions (e.g., vision, hearing and
proprioception)
Monitor patient's emotional, cardiovascular and functional
responses to exercise and position change
Monitor for changes in sensation and orientation, including
presence of content that is violent or self-harmful, changes in
muscle strength, peripheral numbness . . .
Monitor for changes and outliers in lab values which can cause
abnormal neurological manifestations such as altered sensorium
and weakness. This includes: acid-base, fluid and electrolyte,
blood glucose, arterial pH level, PaCO2, HCO3, hyper and
hypokalemia, hyper and hyponatremia, hyper and hypocalcemia,
magnesium and phosphate levels.
Monitor and provide appropriate nursing interventions for
fluctuations and abnormalities in vital signs: pain, fever, oxygen
levels.

2. Safe Environment identify individual safety needs of the patient
remove harmful hazards (e.g. loose rugs, small, moveable
furniture, tubing, electrical cords)
safeguard with side rails/side rail padding as appropriate, low-
height bed, firm mattress
place frequently used objects within reach: call light, bed
positioning switch,
block the patient's view of the bathroom, commode or other
equipment used for elimination
provide appropriate level (and least restrictive) of
supervision/surveillance to monitor patient and to allow for
therapeutic actions, as needed
initiate and maintain precaution status for patient at high risk for
dangers specific to the are setting
communicate information about patient's risk to other nursing
staff
Escort patient to off-ward activities as appropriate 3. Elimination Needs Assess patient's need for toileting every two hours. Assist patient
to toilet/commode/bedpan/fracture pan/urinal at specified
intervals APPENDIX - TABLE 2-continued Intervention Processes Avoid the "I'll be right back" syndrome, and leaving patient on a toilet or commode
Provide appropriate peri and anal care. Assist patient in accomplishing appropriate post-elimination hygiene.
Remove essential clothing to allow for elimination
Instruct patient to respond immediately to urge to void, as appropriate
Instruct patient to empty bladder prior to activity, relevant procedures
Provide enough time for bladder emptying (10 minutes). Monitor for possible urine retention using a bladder scanner or other appropriate means 4. Monitor/Observe Activities/Mobility Perform gait assessment: "Get Up and Go Test" to determine how much assistance is required. Consider a physical therapy consult if very unsteady.
Collaborate with the physician to minimize "bedrest" orders. Bedrest promotes deconditioning in all age groups.
Medicate prior to an activity to increase participation, but evaluate the hazard of sedation
Provide self-care assistance. Encourage independence but intervene when patient is unable to perform
Provide appropriate adaptive mobility devices
Monitor patient's need for adaptive deices for personal hygiene, dressing, grooming, toileting and eating & provide assistance until patient is fully able to assume self-care
Provide adequate rest periods 5. Patient/Family Education instruct patient and family on medication side effects
instruct in availability and usage of assistive devices, if appropriate
instruct patient/caregiver about safe transfer and ambulation techniques
Encourage family to stay with patient, as appropriate
Consult with family to establish patient's pre-injury cognitive baseline
Include family/SO in planning, providing and evaluating care to the extent desired
Teach family about prescribed activity, safety, medication, dietary, elimination and self-care parameters 6. Team Management Collaborate with PT, OT and recreational therapies in developing and executing a mobility and activity program
Collaborate with team to monitor therapeutic effects of the medication
Collaborate with team to monitor for signs and symptoms of drug toxicity, as well as adverse effects of the drug
Monitor serum blood levels (e.g. electrolytes, prothrombin, medications) as appropriate
Collaborate with team members to find the most beneficial diet plan for the patient

The invention claimed is:

1. A system for determining a fall risk of a patient for use by a caregiver, the system comprising:
  a first computer readable storage medium for recording fall risk data of a patient, the fall risk data including the fall risk factors exhibited of confusion, depression, altered elimination, dizziness, male gender, antiepileptic/anticonvulsant prescriptions and benzodiazepine prescriptions;
  a second computer readable storage medium for recording mobility data of the patient, the mobility data including information about the patient's ability to rise from a seated position;
  an input device for enabling a caregiver to enter the fall risk data and the mobility data into the first and second computer readable storage media, wherein the caregiver enters a weighted point value from a predefined point value range for each of the intrinsic fall risk factors exhibited by the patient and a weighted point value from a predefined point value range based upon the patient's ability to rise from a seated position;
  wherein the point values for confusion and the ability to rise from a seated position are the highest weighted point values;
  the point values for altered elimination, dizziness, male gender and benzodiazepine prescriptions are the lowest weighted point values; and
  the remaining intrinsic fall risk factors are each assigned a weighted point value between the highest and lowest weighted point values;
  a processor for summing the weighted point values for the intrinsic fall risk factors and the weighted point value based on the patient's ability to rise from a seated position to achieve a total fall risk score and for determining the patient's fall risk based upon the total fall risk score; and
  a display for communicating the total fall risk score of the patient to the caregiver.

2. The system of claim 1, further comprising a computing station having a user interface for entering the data into at least one of the first and second computer readable storage media.

3. The system of claim 2, further comprising a network for transmitting the data from the computing station to at least one of the first and second computer readable storage media.

4. The system of claim 3, wherein the network is selected from a group including an Internet and an Intranet.

5. The system of claim 1, wherein the input device is selected from at least one of a mouse, a keyboard, an electronic display screen, an electronic stylus and a voice recognition program.

6. The system of claim 1, further comprising a computerized device encoded with computer programming logic that when executed compares a patient's total fall risk score with other total fall risk scores contained within an electronic database to determine fall risk trends.

7. The system of claim 1, further comprising a computerized device encoded with computer programming logic that when executed generates a message to a remote computing station when a patient's total fall risk score is greater than or equal to five.

8. The system of claim 1, further comprising a computerized device encoded with computer programming logic that when executed communicates the total fall risk score of the patient to a caregiver.

9. A computer readable storage medium for use with a fall risk determination system, the storage medium storing instructions that, when executed by a caregiver, cause the fall risk determination system to implement the following steps:
  calculating a total fall risk score of a patient by summing a weighted point value from a predefined point value range based upon the patient's ability to rise from a seated position together with weighted point values from a predefined point value range, each of the weighted point values being individually representative of intrinsic fall risk factors exhibited by the patient of confusion, depression, altered elimination, dizziness, male gender, antiepileptic/anticonvulsant prescriptions and benzodiazepine prescriptions, wherein at least one first intrinsic fall risk factor is assigned a highest weighted point value, at least one second intrinsic fall risk factor is assigned a lowest weighted point value, and the remaining intrinsic fall risk factors are each assigned a weighted point value in between the highest and lowest point values; and communicating the total fall risk score of the patient to the caregiver;

wherein the point value for confusion is the highest weighted point value; the point value for depression is in between the highest weighted point value and the lowest weighted point value; the point value for altered elimination is the lowest weighted point value; the point value for dizziness is the lowest weighted point value; the point value for the male gender is the lowest weighted point value; the point value for an antiepileptic/anticonvulsant prescription is in between the highest weighted point value and the lowest weighted point value; the point value for a benzodiazepine prescription is the lowest weighted point value; and the weighted point value based on the patient's ability to rise from a seated position is the highest weighted point value.

10. The computer readable storage medium of claim 9, wherein the stored instructions, when executed, further cause the fall risk determination system to compare a patient's total fall risk score with other total fall risk scores contained within an electronic database to determine fall risk trends.

11. The computer readable storage medium of claim 9, wherein the stored instructions, when executed, further cause the fall risk determination system to generate a message to a remote computing station when a patient's total fall risk score is greater than or equal to five.

* * * * *